(12) United States Patent
Chen et al.

(10) Patent No.: US 11,724,131 B2
(45) Date of Patent: Aug. 15, 2023

(54) WEARABLE ULTRASONIC THERAPEUTIC DEVICE CONTROLLED BY MOBILE ELECTRONIC DEVICE

(71) Applicants: National Health Research Institutes, Miaoli County (TW); National Yang Ming Chiao Tung University, Hsinchu (TW)

(72) Inventors: Gin-Shin Chen, Miaoli County (TW); Chia-Hsuan Chang, Hsinchu County (TW); Jung-Chih Chen, Hsinchu (TW)

(73) Assignees: NATIONAL HEALTH RESEARCH INSTITUTES, Miaoli County (TW); NATIONAL YANG MING CHIAO TUNG UNIVERSITY, Hsinchu (TW)

(*) Notice: Subject to any disclaimer, the term of this patent is extended or adjusted under 35 U.S.C. 154(b) by 16 days.

(21) Appl. No.: 17/535,327

(22) Filed: Nov. 24, 2021

(65) Prior Publication Data

US 2023/0059663 A1  Feb. 23, 2023

(30) Foreign Application Priority Data

Aug. 17, 2021 (TW) .................................. 110130359

(51) Int. Cl.
*A61N 7/00* (2006.01)
*A61B 8/14* (2006.01)
*A61B 8/00* (2006.01)

(52) U.S. Cl.
CPC .................. *A61N 7/00* (2013.01); *A61B 8/14* (2013.01); *A61B 8/4472* (2013.01); *A61B 8/469* (2013.01); *A61B 8/54* (2013.01)

(58) Field of Classification Search
CPC .................................. A61B 8/54; A61B 8/447
See application file for complete search history.

(56) References Cited

U.S. PATENT DOCUMENTS

| | | | |
|---|---|---|---|
| 2004/0260209 A1* | 12/2004 | Ella | A61H 19/32 601/7 |
| 2006/0149169 A1* | 7/2006 | Nunomura | A61N 7/00 601/2 |
| 2010/0016841 A1* | 1/2010 | De Taboada | A61N 5/0622 606/2 |
| 2010/0222676 A1* | 9/2010 | Ogihara | A61B 8/12 600/439 |

(Continued)

*Primary Examiner* — Joel Lamprecht
*Assistant Examiner* — Nyrobi Celestine
(74) *Attorney, Agent, or Firm* — Chun-Ming Shih; HDLS IPR Services

(57) ABSTRACT

A wearable ultrasonic therapeutic device controlled by a mobile electronic device is provided, which includes a mobile device, at least one ultrasonic probe module and a strap. The mobile device has a mobile device control interface for setting ultrasonic parameters and displaying an echo wave through a specific software interface of the mobile device. The ultrasonic probe module includes at least one ultrasonic transducer and a control circuit corresponding thereto. The ultrasonic transducer generates and receives an ultrasonic wave. The control circuit has the functions of generating/receiving signals, phase regulation, power amplification and matching. One end of the ultrasonic probe module is electrically connected to the mobile device and the other end of the ultrasonic probe module is connected to the strap.

9 Claims, 6 Drawing Sheets

(56) References Cited

U.S. PATENT DOCUMENTS

| | | | |
|---|---|---|---|
| 2012/0277640 A1* | 11/2012 | Lewis, Jr. | A61B 8/4281 |
| | | | 601/2 |
| 2014/0321674 A1* | 10/2014 | Abolfathi | H04R 25/606 |
| | | | 381/151 |
| 2016/0136462 A1* | 5/2016 | Lewis, Jr. | A61N 7/00 |
| | | | 601/2 |
| 2017/0007853 A1* | 1/2017 | Alford | A61B 8/02 |
| 2017/0135671 A1* | 5/2017 | Nowak | A61B 5/4504 |
| 2017/0360413 A1* | 12/2017 | Rothberg | A61B 8/145 |
| 2018/0042659 A1* | 2/2018 | Rupp | A61B 17/320068 |
| 2019/0143149 A1* | 5/2019 | Sverdlik | B06B 3/00 |
| | | | 601/2 |
| 2019/0247680 A1* | 8/2019 | Mayer | A61B 18/1477 |
| 2019/0269943 A1* | 9/2019 | Lewis, Jr. | G10K 11/02 |
| 2020/0163647 A1* | 5/2020 | Hakkens | A61B 8/4281 |
| 2021/0128067 A1* | 5/2021 | Imtiaz | A61B 50/30 |
| 2022/0023668 A1* | 1/2022 | Firouzi | A61N 7/00 |

* cited by examiner

WEARABLE ULTRASONIC THERAPEUTIC DEVICE CONTROLLED BY MOBILE ELECTRONIC DEVICE

BACKGROUND OF THE INVENTION

Field of the Invention

The present invention relates to an ultrasonic device, in particular to a wearable ultrasonic therapeutic device controlled by a mobile electronic device.

The Prior Arts

Currently available ultrasonic therapeutic apparatus is of large size and need a large operation space. Besides, currently available ultrasonic therapeutic apparatus needs to be operated by medical staff and must be connected to the utility power. Thus, these ultrasonic therapeutic apparatuses are usually used in hospitals or clinics for now. Therefore, it has become an important issue to improve these ultrasonic therapeutic apparatuses to make these apparatuses be able to be directly used in people's houses in order to enhance the convenience thereof.

SUMMARY OF THE INVENTION

Therefore, one embodiment of the present invention provides an innovative technology integrating a wearable ultrasonic probe module with a mobile electronic device to control the output of an ultrasonic wave in order to overcome the shortcomings of the prior art. One embodiment of the present invention provides a wearable ultrasonic therapeutic device controlled by a mobile electronic device, which includes a mobile device, an ultrasonic probe module and a strap. The mobile device has a mobile device control interface for setting ultrasonic parameters and displaying an echo wave through a specific software interface of the mobile device. The ultrasonic probe module includes at least one ultrasonic transducer and a control circuit corresponding thereto. The ultrasonic transducer generates and receives an ultrasonic wave. The control circuit has the functions of generating/receiving signals, phase regulation, power amplification and matching. One end of the ultrasonic probe module is electrically connected to the mobile device and the other end of the ultrasonic probe module is connected to the strap. The strap is joined by at least one ring and the ultrasonic transducer is fixed by the ring. The wearable ultrasonic therapeutic device can emit a continuous or pulse ultrasonic wave to the target tissue to be treated.

In one embodiment of the invention, the combination structure of the wearable ultrasonic therapeutic device controlled by the mobile electronic device is selected from the group consisting of a rotation-type combination structure and a push-in-type combination structure. The structure of the rotation-type combination structure includes a lid, a cable, the ultrasonic transducer and a rotation-type shell. The outer surface of the rotation-type shell is provided with at least one combined body. One end of the cable is electrically connected to the ultrasonic transducer and the other end of the cable is electrically connected to the control circuit.

In one embodiment of the invention, the combination structure of the wearable ultrasonic therapeutic device controlled by the mobile electronic device is selected from the group consisting of the rotation-type combination structure and the push-in-type combination structure. The push-in-type combination structure includes a lid, a cable, the ultrasonic transducer and a push-in-type shell. The ultrasonic transducer is disposed on the push-in-type shell. One end of the cable is electrically connected to the ultrasonic transducer and the other end of the cable is electrically connected to the control circuit.

In one embodiment of the invention, the ultrasonic probe module is fixed on the strap via the ring, which includes an upper combined ring and a lower combined ring. The upper combined ring is hollow and ring-shaped. The upper combined ring is configured to accommodate the rotation-type shell. The inner surface of the upper combined ring has at least one convex body, such that the convex body is engaged with the combined body after the upper combined ring is combined with the rotation-type shell. The lower combined ring is hollow and ring-shaped. The lower combined ring is configured to accommodate the rotation-type shell. The strap has at least one hole corresponding to the upper combined ring and the lower combined ring to accommodate the rotation-type shell, and the strap is clamped between the upper combined ring and the lower combined ring by at least one lock piece.

In one embodiment of the invention, wherein the ultrasonic probe module is fixed on the strap via the ring, which includes: an upper push-in ring and a lower combined ring. The upper push-in ring is hollow and ring-shaped. The upper push-in ring is configured to accommodate the push-in-type shell. The outer surface of the upper push-in ring has at least one hook-like body configured to push-in the push-in-type shell to the upper push-in ring. The lower combined ring is hollow and ring-shaped. The lower combined ring is configured to accommodate the push-in-type shell. The strap has at least one hole corresponding to the upper push-in ring and the lower combined ring to accommodate the push-in-type shell, and the strap is clamped between the upper push-in ring and the lower combined ring by at least one lock piece.

In one embodiment of the invention, each of the two sides of the strap is provided with an adhesive sheet, and the strap is fixed by the adhesive sheets after the adhesive sheets are sticked to each other.

In one embodiment of the invention, the mobile device control interface has a waveform setting key configured to set at least one waveform of the ultrasonic wave emitted by the ultrasonic transducer.

In one embodiment of the invention, the ultrasonic probe module has at least one ultrasonic transducer and the control circuit corresponding thereto, the parameters of the ultrasonic transducer emitting the ultrasonic wave are set by a channel parameter setting key of the mobile device control interface. The parameters may include as frequency, duty cycle, power and phase.

In one embodiment of the invention, the mobile device control interface includes a time module. The time module includes a starting key, a stop key and a reset key. The starting key is configured to set the emission duration of the ultrasonic transducer emitting the ultrasonic wave, and start the ultrasonic transducer to emit the ultrasonic wave. When the emission duration ends, the ultrasonic transducer stops emitting the ultrasonic wave. The stop key is configured to control the ultrasonic transducer to stop emitting the ultrasonic wave during the emission duration. When the starting key is pressed again, the ultrasonic transducer continues to emit the ultrasonic wave until a remainder of the emission duration ends. The reset key is configured to reset the emission duration after the stop key stops the ultrasonic transducer to emit the ultrasonic wave.

In one embodiment of the invention, the control circuit, includes a processor, a phase controller, at least one channel, at least one power amplifier and at least one impedance matching circuit. The processor is configured to control the frequency, the duty cycle, the power, and the waveform of the ultrasonic wave, and the processor is electrically connected to the mobile device control interface. One end of the phase controller is electrically connected to the processor and the phase controller has an output end connected to the input end of the channel, which can control the phase of ultrasonic wave. The other end of the phase controller is electrically connected to the power amplifier. One end of the impedance matching circuit is electrically connected to the other end of the power amplifier and the other end of the impedance matching circuit is electrically connected to the ultrasonic transducer.

In one embodiment of the invention, the mobile device control interface simultaneously sets the waveform setting key, the channel parameter setting key and the time module so as to simultaneously control at least one or the combination of two or more of the channel, the frequency, the duty cycle, the power, the phase, the waveform and the time corresponding to the ultrasonic wave emitted by the ultrasonic transducer.

In one embodiment of the invention, wherein the ultrasonic transducer is made of piezoelectric material. The ultrasonic transducer can not only generate the ultrasonic wave by electrical excitation, but also can detect the echo wave reflected from the contact surface between the ultrasonic transducer and the skin of a person. The echo wave is converted into an electrical signal via the ultrasonic transducer and the electrical signal is processed by the echo wave receiver electrically connected to the mobile device. The mobile device displays the electrical signal on the mobile device control interface. The strength of this echo wave can be used to confirm whether the surface of the ultrasonic transducer contacts the skin.

The technical means adopted by the wearable ultrasonic therapeutic device controlled by the mobile electronic device of the present invention may be different from those of the hand-held ultrasonic therapeutic device. The ultrasonic therapeutic device according to the embodiments of the present invention is wearable and the therapeutic depth thereof is adjustable. The wearable ultrasonic therapeutic device can be installed with one or more ultrasonic probe modules by rotating or processing the ultrasonic probe module(s), which can conform to the requirements of different applications and be more convenient in operation. In addition, the wearable design and the mobile device control interface thereof allow the user to operate the device by himself/herself without supporting from other people. The ultrasonic transducer of a currently available ultrasonic therapeutic device cannot be driven without being connected to utility power. On the contrary, the ultrasonic transducer of the ultrasonic therapeutic device according to the embodiments of the present invention can be driven by the power supply of 5V to 20V. According to the embodiments of the present invention, the ultrasonic transducer for therapeutic purpose is driven by the mobile device to generate ultrasonic waves having different waveforms, including continuous waves (e.g., sine waves, square waves) and pulse waves (e.g., pulse waves, pulse string waves), etc. The function of the signal generator is controlled by the mobile device in order to set the frequency, duty cycle, pulse width and so on. According to the embodiments of the present invention, the frequency of the ultrasonic transducer for therapeutic purpose can be adjusted between 0.5 MHz and 7 MHz (bandwidth 1 MHz) and the ultrasonic transducers having different sizes can be combined to change the transmission depth of the ultrasonic waves thereof. According to the embodiments of the present invention, the phase of the ultrasonic wave can be adjusted by the mobile device by performing phase control so as to adjust the focus position. According to the embodiments of the present invention, the ultrasonic transducer can be used to emit the ultrasonic wave, and then detect and record the echo wave thereof. In addition, the ultrasonic wave treatment can be applied to pain management, rehabilitation, neuromodulation or health care; the treatment course is usually several minutes per time, several times per week, which can last several weeks. The wearable ultrasonic therapeutic device according to the embodiments of the present invention is of small size, light weight and convenient to wear. Besides, the treatment course and the dosage of the ultrasonic wave can be realized by an App, so can be controlled by a mobile device. Thus, the wearable ultrasonic therapeutic device is quite suitable for people to use in their houses. The wearable ultrasonic therapeutic device emits the ultrasonic wave to the target tissue to be treated for physical therapy and the dosage of the ultrasonic wave is adjustable.

DETAILED DESCRIPTION OF THE PREFERRED EMBODIMENT

Figure 1A:
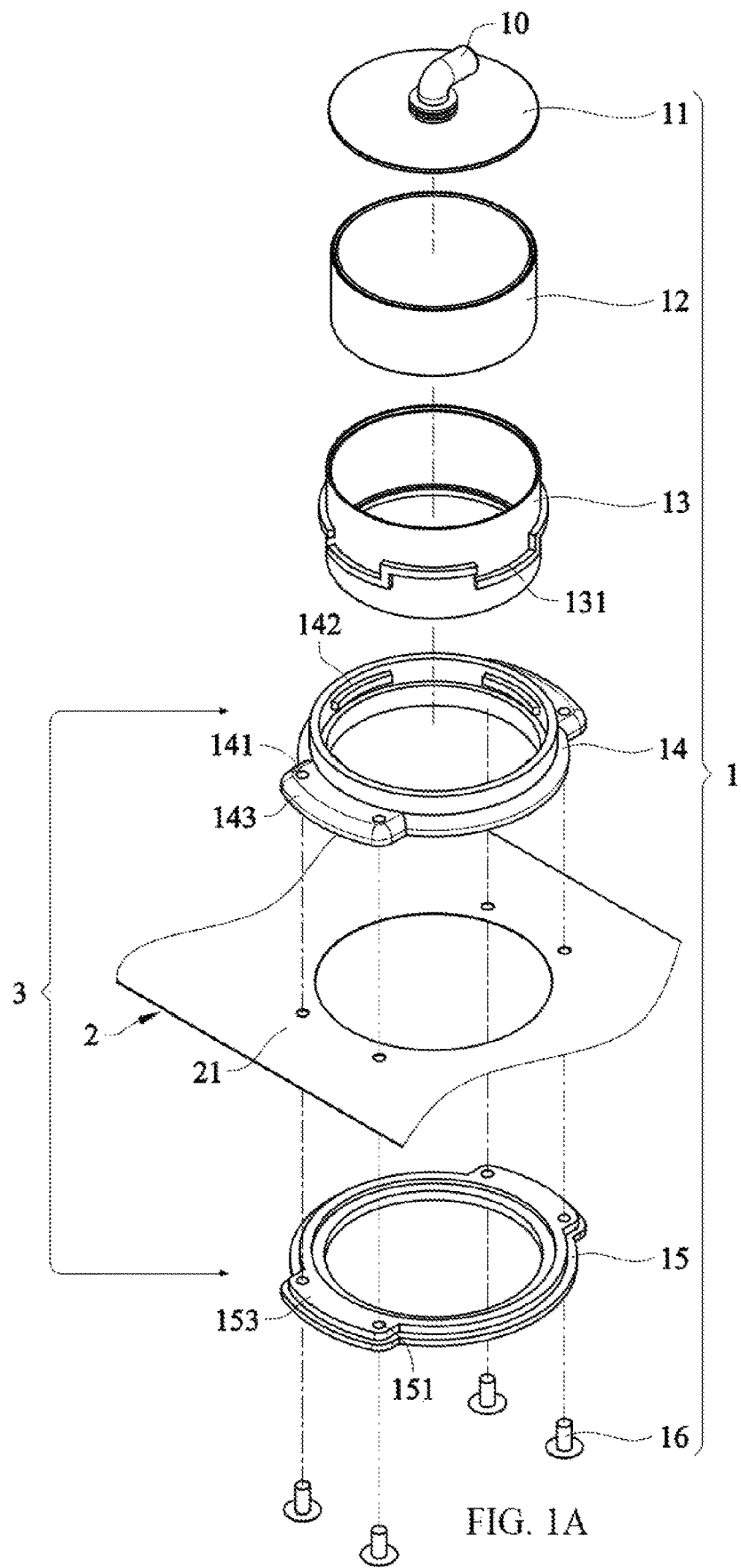
FIG. 1A is an exploded view of an ultrasonic component in accordance with a first embodiment of the present invention.
Figure 1B:
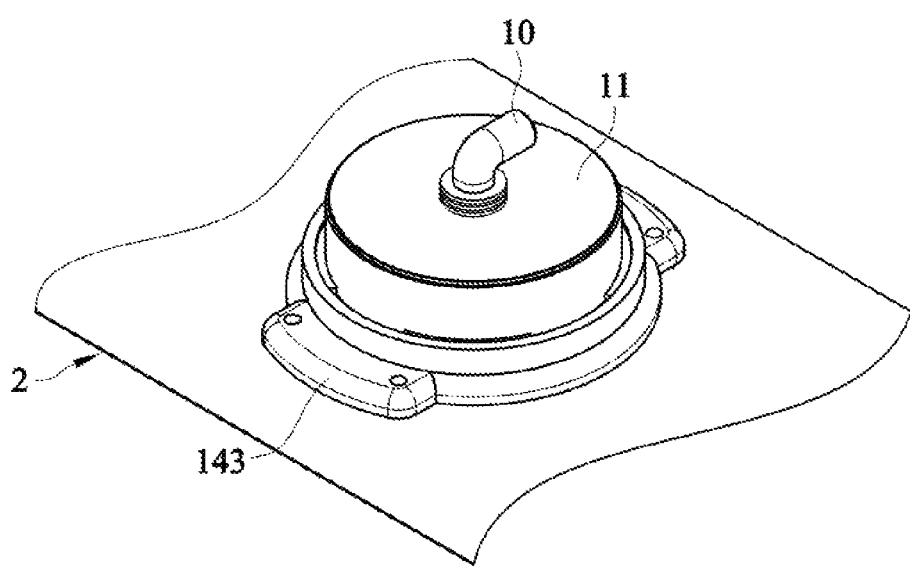
FIG. 1B is an assembly view of the ultrasonic component in accordance with the first embodiment of the present invention.

FIG. 1A and FIG. 1B show a wearable ultrasonic therapeutic device controlled by a mobile electronic device in accordance with a first embodiment of the present invention. As shown in FIG. 1A and FIG. 1B, the combination structure of the ultrasonic component 1 is a rotation-type combination structure, which includes a lid 11, a cable 10, an ultrasonic transducer 12, a rotation-type shell 13 and a ring 3. The ultrasonic transducer 12 is disposed in the rotation-type shell 13 and the outer surface of the rotation-type shell 13 has at least one combined body 131; one end of the cable 10 is electrically connected to the ultrasonic transducer 12 and the other end of the cable 10 is electrically connected to the control circuit 65. The ring 3 includes an upper combined ring 14 and a lower combined ring 15. The upper combined ring 14 is hollow and ring-shaped. The upper combined ring 14 is configured to accommodate the rotation-type shell 13. The inner surface of the upper combined ring 14 has at least one convex body 142, such that the convex body 142 is engaged with the combined body 131 of the rotation-type shell 13. The lower combined ring 15 is hollow and ring-shaped. The lower combined ring 15 is configured to accommodate the rotation-type shell 13. The strap 2 has at least one hole 151 corresponding to the upper combined ring 14 and the lower combined ring 15 to accommodate the rotation-type shell 13. The strap 2 is clamped between the upper combined ring 14 and the lower combined ring 15 by at least one lock piece 16. As shown in FIG. 1A and FIG. 1B, the lock piece 16 can effectively achieve the above clamping effect via the ring holes 141 of the upper fixing piece 143, the holes 21 of the strap 2 and the holes 151 of the lower fixing piece 153.

Figure 2A:
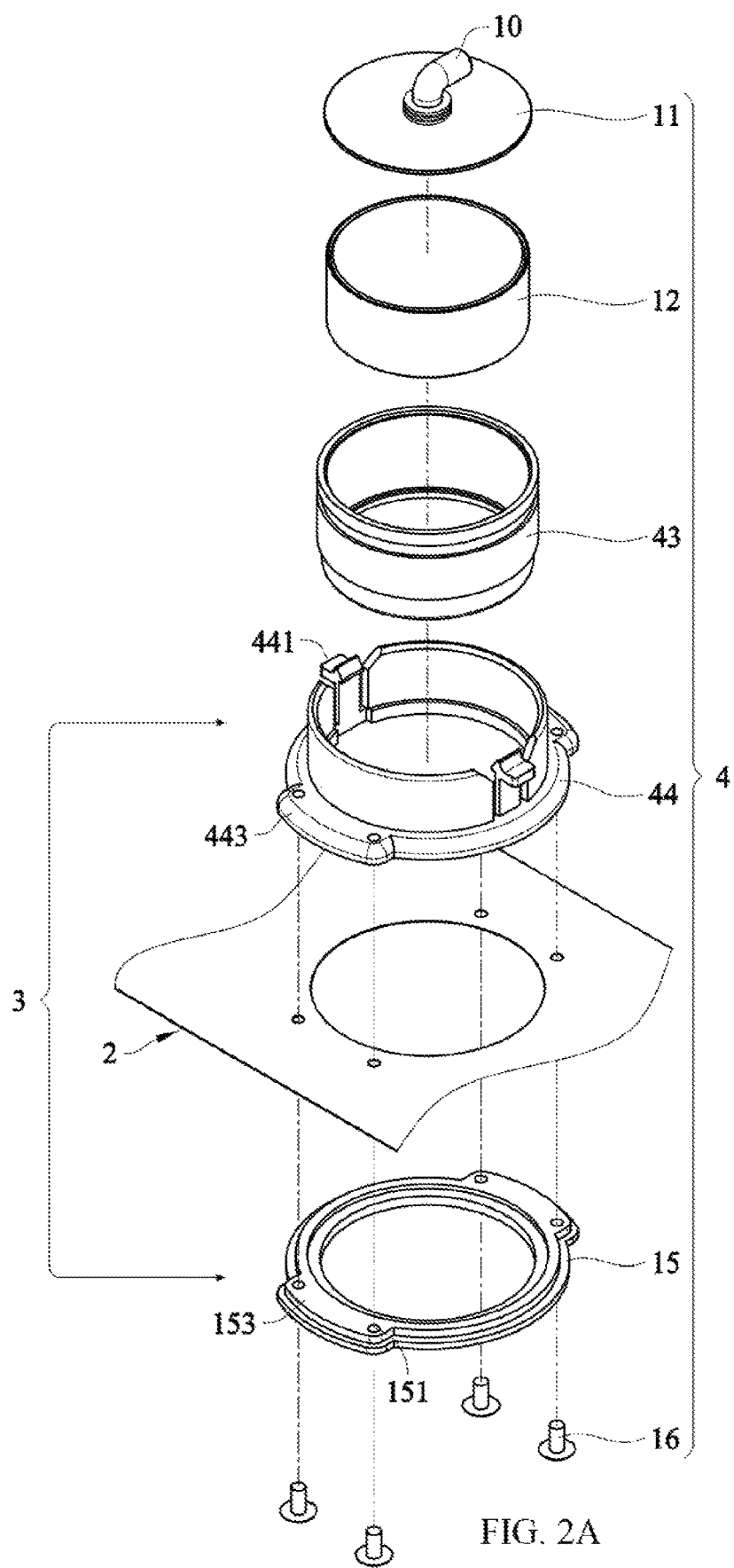
FIG. 2A is an exploded view of an ultrasonic component in accordance with a second embodiment of the present invention.
Figure 2B:
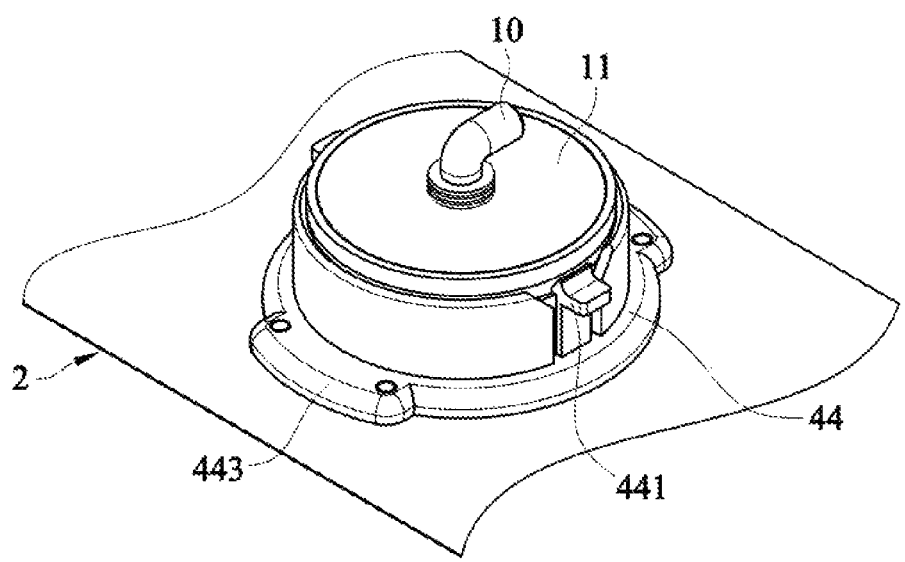
FIG. 2B is an assembly view of the ultrasonic component in accordance with the second embodiment of the present invention.

FIG. 2A and FIG. 2B show a wearable ultrasonic therapeutic device controlled by a mobile electronic device in accordance with a second embodiment of the present invention. As shown in FIG. 2A and FIG. 2B, the combination structure of the ultrasonic component 4 is a push-in-type combination structure, which includes a lid 11, a cable 10, an ultrasonic transducer 12, a push-in-type shell 43 and a ring 3. The ultrasonic transducer 12 is disposed in the push-in-type shell 43. One end of the cable 10 is electrically connected to the ultrasonic transducer 12 and the other end of the cable 10 is electrically connected to the control circuit 65. The ring 3 includes an upper push-in ring 44 and a lower combined ring 15. The upper push-in ring 44 is hollow and ring-shaped. The upper push-in ring 44 is configured to accommodate the push-in-type shell 43 and the outer surface of the upper push-in ring 44 has at least one hook-like body 441 configured to clamp the push-in-type shell 43 to the upper push-in ring. The lower combined ring 15 is hollow and ring-shaped. The lower combined ring 15 is configured to accommodate the push-in-type shell 43. The strap 2 has at least one hole 151 corresponding to the upper push-in ring 44 and the lower combined ring 15 to accommodate the push-in-type shell 43. The strap 2 is clamped between the upper push-in ring 44 and the lower combined ring 15 by at least one lock piece 16. As shown in FIG. 2A and FIG. 2B, the lock piece 16 can effectively achieve the above clamping effect via the ring holes 141 of the upper fixing piece 443, the holes 21 of the strap 2 and the holes 151 of the lower fixing piece 153.

Figure 3A:
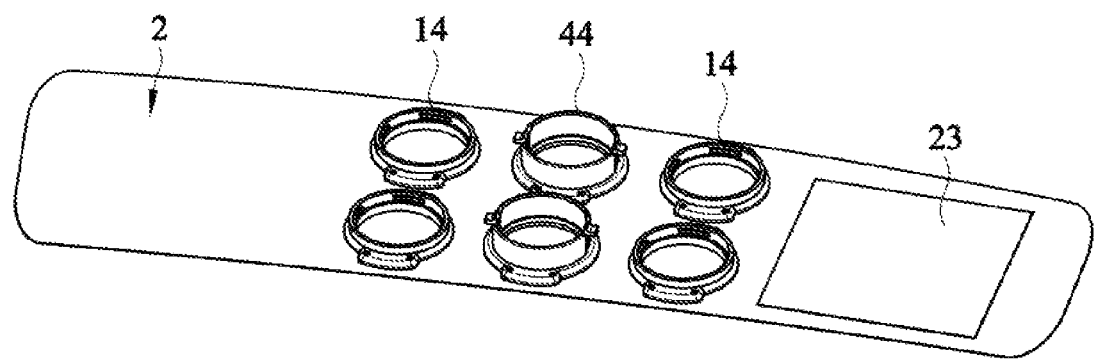
FIG. 3A is a top view of an ultrasonic component combined with a strap in accordance with a third embodiment of the present invention.
Figure 3B:
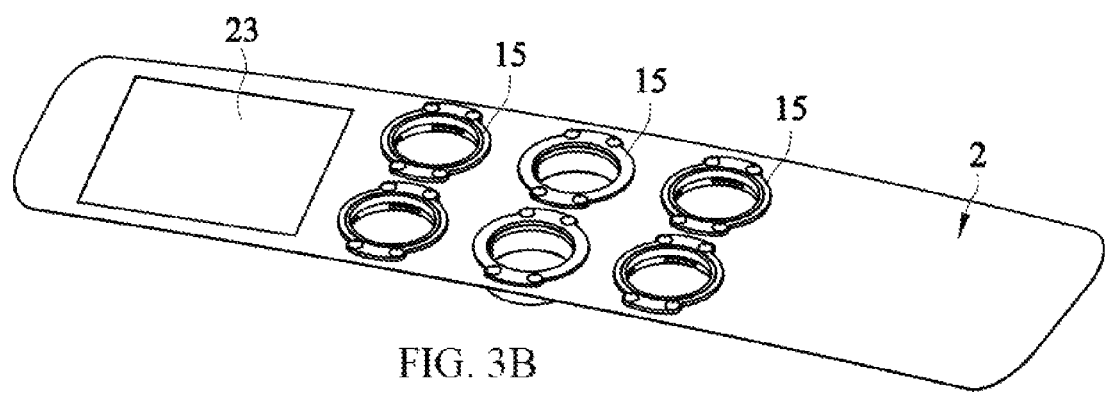
FIG. 3B is a bottom view of the ultrasonic component combined with the strap in accordance with the third embodiment of the present invention.
Figure 3C:
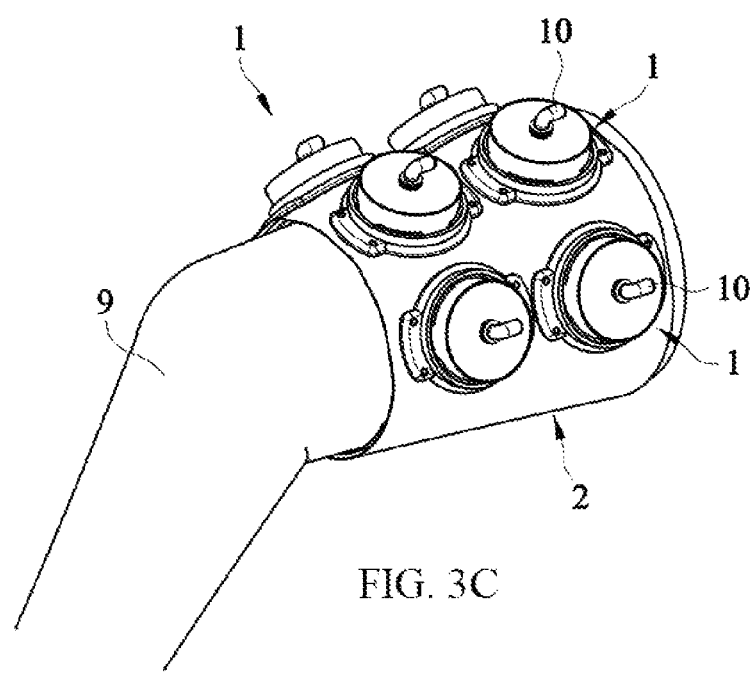
FIG. 3C is a schematic view of a person wearing the strap on his thigh in accordance with the third embodiment of the present invention.

FIG. 3A, FIG. 3B and FIG. 3C show a wearable ultrasonic therapeutic device controlled by a mobile electronic device in accordance with a third embodiment of the present invention. As shown in FIG. 3A, FIG. 3B and FIG. 3C, a person wears a strap 2 on at least one target tissue 73 to be treated. In this embodiment, the person wears the strap 2 on his/her thigh 9. Each of the two sides of the strap 2 is provided with an adhesive sheet 23 and the strap 2 is fixed on the thigh 9 by the adhesive sheets 23 after the adhesive sheets 23 are sticked to each other. As shown in the top view of the ultrasonic probe module 60 combined with the strap 2, the combination structure of the ultrasonic probe module 60 may be one of the rotation-type combination structure and the push-in-type combination structure. Regarding the rotation-type combination structure, the rotation-type shell 13, the upper combined ring 14, the strap 2 and the lower combined ring 15 can be combined with each other, and then the inner surface of the upper combined ring 14 has at least one convex body 142, such that the convex body 142 is engaged with the combined body 131 after the upper combined ring 14 is combined with the rotation-type shell 13. Regarding the push-in-type combination structure, the push-in-type shell 43, the upper push-in ring 44, the strap 2 and the lower combined ring 15 can be combined with each other, and then the outer surface of the upper push-in ring 44 has at least one hook-like body 441 configured to clamp the push-in-type shell 43 to the upper push-in ring 44. In this embodiment, there may be several ultrasonic components 1 disposed on the strap 2. Besides, the combination structures of these ultrasonic components 1 may include only the rotation-type combination structure, or include only the push-in-type combination structure, or include both of which. Further, the ultrasonic components 1 may be arranged in a straight line or to form an array. The strap 2 may be made of nylon or mixed fabric; the surface contacting the skin of the patient may be made of cotton or imitation velvet fabric with better touch. After the body part, of the patient, to be treated is wrapped by the strap 2, the strap 2 can be fixed by the adhesive layers 23.

Figure 4:
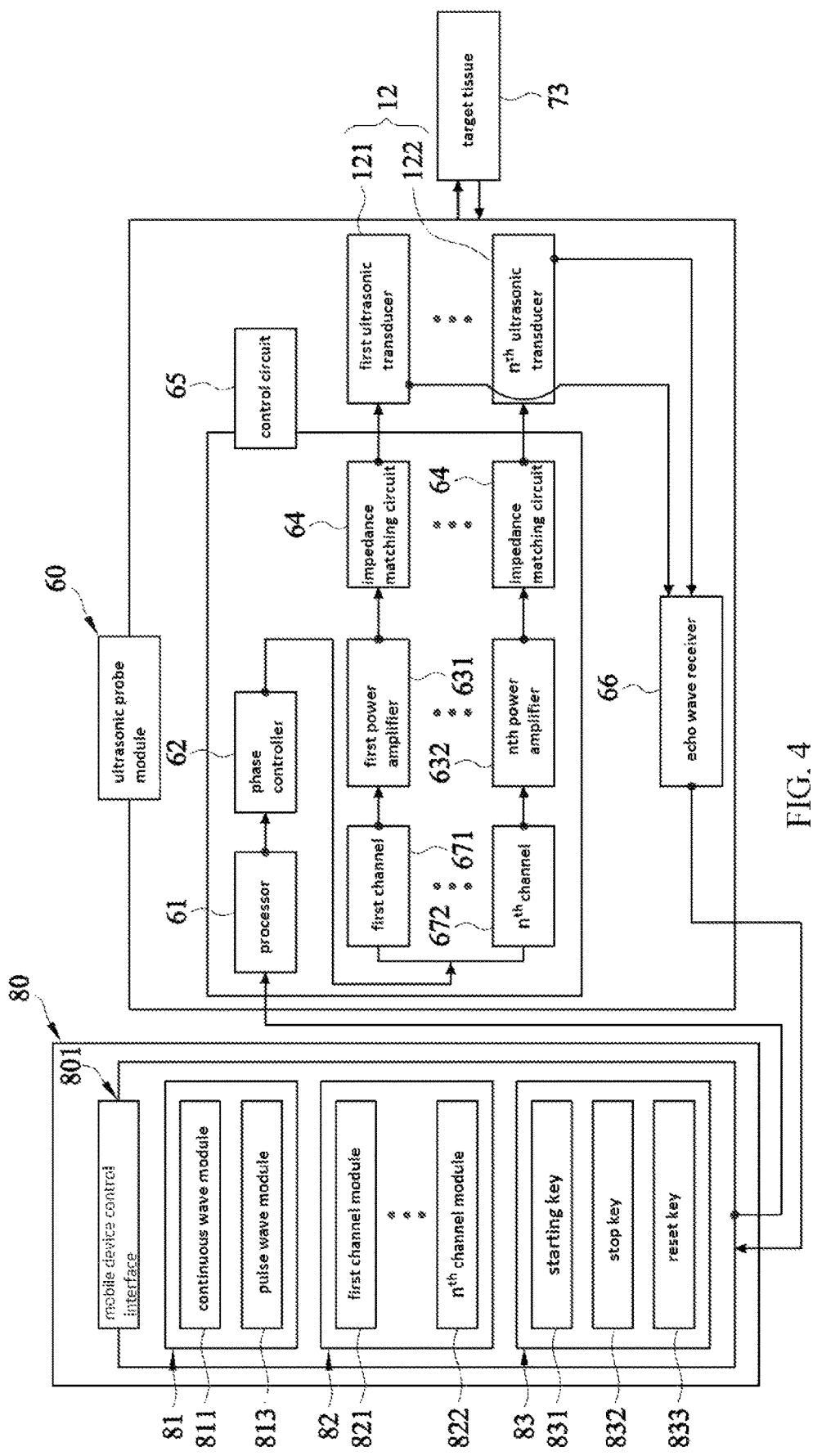
FIG. 4 is a schematic view of a wearable ultrasonic therapeutic device controlled by a mobile electronic device in accordance with a fourth embodiment of the present invention.

As shown in FIG. 1A, FIG. 1B, FIG. 2A, FIG. 2B, FIG. 3C and FIG. 4, the ultrasonic transducer 12 can convert the electrical energy into mechanical energy and the range of the operating frequency thereof is between 0.5 MHz and 7 MHz. The operating frequency of the ultrasonic transducer 12 can be adjusted according to different applications. For example, the ultrasonic transducer 12 can be applied to treat the pain due to peripheral neuropathy and the frequency thereof can be set to be 2 MHz to 7 MHz. The ultrasonic transducer 12 can be applied to rehabilitation and the frequency thereof can be set to be 0.5 MHz to 1 MHz. The ultrasonic transducer 12 can also be applied to neuromodulation and the frequency thereof can be set to be 1 MHz to 3 MHz. The ultrasonic transducer 12 may be disc-shaped or bowl-shaped. The aperture of a disc-shaped ultrasonic transducer 12 is 1 cm to 2 cm and the thickness of the disc-shaped ultrasonic transducer 12 is determined according to the operating frequency thereof. For instance, if the frequency of the disc-shaped ultrasonic transducer 12 is 1 MHz or 2 MHz, the thickness thereof is 2 mm or 1 mm. If the ultrasonic transducer 12 is bowl-shaped, the aperture thereof is 1 cm to 5 cm and the f number obtained by dividing the radius of curvature thereof by the aperture is 0.6 to 1.2. The ultrasonic transducer 12 may be made of a ceramic piezoelectric material or a piezoelectric composite material, such as PZT 4 or PZT 8 or PZT filled resin composite material. In the embodiments of the present invention, the cable 10 may be a coaxial cable; the live wire and the ground wire thereof are respectively connected with the positive electrode and the negative electrode of ultrasonic transducer 12. The lid 11 has a reserved hole for the cable 10 to pass through. The components of the ultrasonic probe module 60 can be protected by the combination structure 1 or 4 so as to achieve insulation effect and waterproof effect. As shown in FIG. 4, the ultrasonic probe module 60 includes a control circuit 65, the ultrasonic transducer 12 and an echo wave receiver 66. The control circuit 65 includes a processor 61, a phase controller 62, $1^{st} \sim n^{th}$ power amplifier 631~632 and an impedance matching circuit 64.

In general, most of ultrasonic transducer for therapeutic purpose should be powered by the utility power. As shown in FIG. 4, according to the embodiments of the present invention, the power supply portion of the wearable ultrasonic therapeutic device is about 5 V to 20 V, and the wearable ultrasonic therapeutic device can be charged via the charging port of the mobile phone or a wireless charger. The control circuit of the wearable ultrasonic therapeutic device can be provided with a wireless charging IC to provide wireless charging function, so the wearable ultrasonic therapeutic device can be charged by a wireless charging pad. The control circuit of the wearable ultrasonic therapeutic device can be further provided with a DC/DC converter IC for boosting charging if necessary.

As shown in FIG. 4, in these embodiments, the mobile device 80 has a waveform setting key 81, a transmitting/receiving channel module and a time module 83. The waveform setting key 81 is configured to set at least one of the frequency ranges and the waveform of the ultrasonic transducer 12 emitting the ultrasonic wave. Regarding generating control signal, the clocks of some ICs of microcontrollers can be up to MHz-level and can directly produce MHz-level square waves, but some ICs of microcontroller cannot directly produce MHz-level sine waves or square waves. However, according to the embodiments of the present invention, the pulse width modulation (PWM) signal can be controlled via the timer of the processor 61 in the control circuit 65 to change the output frequency and the duty cycle of the PWM signal. The waveform setting key 81 has a continuous wave module 811 and a pulse wave module 813.

As shown in FIG. 4, in these embodiments, the channel parameter setting key 82 has at least one channel module (821, 822), Accordingly, the phase and the power of the ultrasonic transducer 12 transmitting the ultrasonic wave can be set via the channel modules. Further, the ultrasonic wave received by the ultrasonic transducer 12 or the echo wave, of the ultrasonic wave, received by the echo wave receiver 66 can also be set by the channel modules. As shown in FIG. 4, the channel parameter setting key 82 has the $1^{st}$~$n^{th}$ channel modules 821~822.

As shown in FIG. 4, in these embodiments, the ultrasonic transducer 12 has $1^{st}$~$n^{th}$ ultrasonic transducer 121~122. As set forth above, the channel parameter setting key 82 has at least one channel module (821, 822). For example, $1^{st}$~$n^{th}$ ultrasonic transducer 121~122 can be set to receive the echo wave of the emitted ultrasonic wave for therapeutic purpose. Via the piezoelectric effect provided by the piezoelectric material of the ultrasonic transducer 12, when the echo wave, reflected from an object, of the emitted ultrasonic wave returns to the piezoelectric plate of the ultrasonic transducer 12, the echo wave is converted into an electrical signal. Then, the influence of the ultrasonic wave to the object or the absorbing status of the object absorbing the ultrasonic wave can be indirectly monitored according to the amplitude of the electrical signal. The built-in $1^{st}$~$n^{th}$ receiving channels of the echo wave receiver 66 can respectively receive the echo waves corresponding to the $1^{st}$~$n^{th}$ ultrasonic transducer 121~122. The received echo waves can be transmitted back to the channel parameter setting key 82 of the mobile device 80 via the transmission line or Bluetooth. In this way, the user can observe the echo waves via the mobile device 80. Therefore, the channel parameter setting key 82 according to the embodiments of the present invention can be set to emit the ultrasonic wave and receive the echo wave at the same time.

As shown in FIG. 4, in these embodiments, the mobile device 80 has the time module 83, which includes a starting key 831, a stop key 832 and a reset key 833. The starting key 831 is configured to activate the ultrasonic transducer 12 to emit the ultrasonic wave. After the emission duration ends, the ultrasonic transducer 12 stops emitting the ultrasonic wave. The stop key 832 is configured to the ultrasonic transducer 12 to stop emitting the ultrasonic wave during the emission duration. After the ultrasonic transducer 12 stops emitting the ultrasonic wave. The ultrasonic transducer 12 can continue to emit the ultrasonic wave until the remainder of the emission duration ends when the starting key 831 is pressed again. The reset key 833 is configured to reset the emission duration of the ultrasonic transducer 12 emitting the ultrasonic wave.

As shown in FIG. 4, in this embodiment, the control circuit 65 includes a processor 61, a phase controller 62, a power amplifier 63 and an impedance matching circuit 64. One end of the processor 61 may be wirelessly connected to the mobile device 80 or connected to the mobile device 80 via a cable. Regarding the transmission of the control signal, the mobile device 80 transmits the control signal to the processor 61 of the control circuit 65 via Bluetooth, which may be, but not limited to, a microcontroller (MCU). In addition, the control signal can also be transmitted to the processor 65 of the control circuit 65 via the signal cable connected to the transmission port of the mobile device 80. Therefore, according to the embodiments of the present invention, the ultrasonic wave for therapeutic purpose can be generated via wireless means or wired means. The processor 61 controls the frequency, the duty cycle and the waveform of the ultrasonic wave. One end of the phase controller 62 is electrically connected with the processor 61 and the phase controller 62 controls the phase of the ultrasonic wave; the other end of the phase controller 62 is electrical connected with the power amplifier 63. Moreover, one end of the impedance matching circuit 64 is electrically connected to the other end of the phase controller 62 and the other end of the impedance matching circuit 64 is electrically connected to the ultrasonic transducer 12.

As shown in FIG. 4, in these embodiments, the phase controller 62 can adopt field programmable logic gate array (Field Programmable Gate Array, FPGA) and digital circuit design. The shift register is the main design component, which can execute the modulation of phase changes. When the ultrasonic transducer 12 is an array transducer, such as a linear array transducer or a phase array transducer, the phase control parameters thereof can be set via the channel modules. The $1^{st}$ channel module 821 can set the phase of each element of the $1^{st}$ ultrasonic transducer 121. For instance, the $1^{st}$ ultrasonic transducer 121 is a phase array transducer having 128 elements, the 128 phases corresponding to the elements can be set by the $1^{st}$ channel module 821. The phase modulation of the $2^{nd}$ ultrasonic transducer can be set by the $2^{nd}$ channel module. Similarly, the phases of the elements of the $n^{th}$ ultrasonic transducer 122 can be set by the $n^{th}$ channel module 822. The Field Programmable Gate Array (FPGA) can adjust the phases of the signals and then output the signals according to the values set by the channel modules, such that the position of the focus point of each ultrasonic transducer can be adjusted.

As shown in FIG. 4, in these embodiments, the power amplifier 63 may be a Class-D power amplifier 63, which can amplify the power of the ultrasonic wave. The Class-D power amplifier 63 is a switching-type amplifier, which takes a transistor as a switch. The front-end circuit thereof adopts pulse width modulation technology; the middle circuit thereof adopts a half-bridge output stage connected to a filter circuit. According to the embodiments of the present invention, the transistor may be, but not limited to a Power MOSFET; the output voltage thereof can be up to several hundred volts so as to perform power amplification.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A wearable ultrasonic therapeutic device controlled by a mobile electronic device, comprising:
   a mobile device, configured to set ultrasonic parameters and display echo waves via a mobile device control interface;
   at least one ultrasonic probe module, comprising at least one ultrasonic transducer, a control circuit and an echo wave receiver corresponding thereto, wherein the ultrasonic transducer is configured to generate and receive an ultrasonic wave, wherein the control circuit has functions of generating driving signals, phase regulation, power amplification and impedance matching, and the echo wave receiver is configured to collect the echo wave received by the ultrasonic transducer, and one end of the at least one ultrasonic probe module is electrically connected to the mobile device; and
   a strap, wherein the other end of the at least one ultrasonic probe module is connected to the strap, the strap is joined by at least two rings, and the ultrasonic transducer corresponding to the least two rings is fixed by the at least two rings;
   wherein the wearable ultrasound therapeutic device controlled by the mobile electronic device is configured to emit a continuous or pulse ultrasonic wave to a target tissue to be treated;
   wherein a combination structure of the wearable ultrasonic therapeutic device controlled by the mobile electronic device is a rotation-type combination structure or a push-in-type combination structure, wherein when the combination structure is the rotation-type combination structure, the rotation-type combination structure comprises:
   a lid, a cable, the ultrasonic transducer, and a rotation-type shell, wherein the ultrasonic transducer is disposed in the rotation-type shell, and an outer surface of the rotation-type shell is provided with at least one combined body, wherein one end of the cable is electrically connected to the ultrasonic transducer and the other end of the cable is electrically connected to the control circuit; and
   the at least two rings, comprising: an upper combined ring and a lower combined ring, wherein
   the upper combined ring is hollow and ring-shaped, wherein the upper combined ring is configured to accommodate the rotation-type shell, wherein an inner surface of the upper combined ring has at least one convex body, such that the at least one convex body is engaged with the at least one combined body after the upper combined ring is combined with the rotation-type shell; and
   a lower combined ring is hollow and ring-shaped, wherein the lower combined ring is configured to accommodate the rotation-type shell;
   wherein, the strap has at least one hole corresponding to the upper combined ring and the lower combined ring to accommodate the rotation-type shell, and the strap is clamped between the upper combined ring and the lower combined ring by at least one lock piece.

2. The wearable ultrasonic therapeutic device controlled by the mobile electronic device as claimed in claim 1, wherein the control circuit comprises:
   a processor, electrically connected to the mobile device control interface and configured to control a frequency, a duty cycle, a power and a waveform of the ultrasonic wave;
   a phase controller, wherein one end of the phase controller is electrically connected to the processor and the phase controller is configured to control a phase of the ultrasonic wave;
   at least one channel, where an input end of the at least one channel is electrically connected to an output end of the phase controller;
   at least one power amplifier, wherein the other end of the at least one channel is electrically connected to one end of the at least one power amplifier corresponding thereto and the other end of the at least one power amplifier is electrically connected to the ultrasonic transducer corresponding thereto; and
   at least one impedance matching circuit, wherein one end of the at least one impedance matching circuit is electrically connected to the other end of the at least one power amplifier and the other end of the at least one impedance matching circuit is electrically connected to the ultrasonic transducer.

3. The wearable ultrasonic therapeutic device controlled by the mobile electronic device as claimed in claim 2, wherein the at least one ultrasonic probe module comprises:
   the echo wave receiver, wherein one end of the echo wave receiver is electrically connected to the ultrasonic transducer, the other end of the echo wave receiver is electrically connected to the mobile device,
   wherein the ultrasonic transducer is made of piezoelectric material, and generates the ultrasonic wave by electrical excitation, and detects the echo wave reflected from a contact interface between the ultrasonic transducer and the target tissue to be treated,
   wherein the echo wave is converted into an electrical signal via the ultrasonic transducer,
   wherein after the electrical signal is processed by the echo wave receiver, which is electrically connected to the mobile device, the mobile device displays the electrical signal on the mobile device control interface in order to determine whether a surface of the ultrasonic transducer contacts a skin or not.

4. The wearable ultrasonic therapeutic device controlled by the mobile electronic device as claimed in claim 3, wherein a signal transmission between the mobile device control interface and the echo wave receiver is achieved by a wireless connection or wired connection between the mobile device and the at least one ultrasonic probe module.

5. The wearable ultrasonic therapeutic device controlled by a mobile electronic device as claimed in claim 1, wherein when the combination structure is the push-in-type combination structure, the push-in-type combination structure comprises:
   the lid, the cable, the at least one ultrasonic transducer, and a push-in-type shell, wherein the at least one ultrasonic transducer is disposed in the push-in-type shell, wherein one end of the cable is electrically connected to the at least one ultrasonic transducer and the other end of the cable is electrically connected to the control circuit; and
   the at least two rings, comprising an upper push-in ring and the lower combined ring, wherein
   the upper push-in ring is hollow and ring-shaped, wherein the upper push-in ring is configured to accommodate the push-in-type shell and an outer surface of the upper push-in ring has at least one hook-like body configured to clamp the push-in-type shell to the upper push-in ring; and the lower combined ring is hollow and ring-shaped, wherein the lower push-in ring is configured to accommodate the push-in-type shell;

wherein, the strap has at least one hole corresponding to the upper push-in ring and the lower combined ring to accommodate the push-in-type shell, and the strap is clamped between the upper push-in ring and the lower combined ring by at least one lock piece.

6. The wearable ultrasonic therapeutic device controlled by the mobile electronic device as claimed in claim 1, wherein each of two sides of the strap is provided with an adhesive sheet, and the strap is fixed by the adhesive sheets after the adhesive sheets are stuck to each other.

7. The wearable ultrasonic therapeutic device controlled by the mobile electronic device as claimed in claim 1, wherein the mobile control interface comprises:

a waveform setting key, configured to set at least one waveform of the ultrasonic wave emitted by the at least one ultrasonic transducer; and at least one channel parameter setting key, configured to set parameters of emitting the ultrasonic wave, wherein the parameters comprise a channel, a frequency, a duty cycle, a power and a phase.

8. The wearable ultrasonic therapeutic device controlled by the mobile electronic device as claimed in claim 7, wherein the mobile device control interface further comprises a time module and the time module comprises:

a starting key, configured to set an emission duration of the at least one ultrasonic transducer emitting the ultrasonic wave, and start the at least one ultrasonic transducer to emit the ultrasonic wave, wherein when the emission duration ends, the at least one ultrasonic transducer stops emitting the ultrasonic wave;

a stop key, configured to control the at least one ultrasonic transducer to stop emitting the ultrasonic wave during the emission duration, wherein when the starting key is pressed again, the at least one ultrasonic transducer continues to emit the ultrasonic wave until a remainder of the emission duration ends; and a reset key, configured to reset the emission duration after the stop key stops the at least one ultrasonic transducer to emit the ultrasonic wave.

9. The wearable ultrasonic therapeutic device controlled by the mobile electronic device as claimed in claim 8, wherein the mobile device control interface simultaneously sets the waveform setting key, the at least one channel parameter setting key and the time module so as to simultaneously control at least one or a combination of two or more of the channel, the frequency, the duty cycle, the power, the phase, the waveform and time corresponding to the ultrasonic wave emitted by the at least one ultrasonic transducer.

* * * * *